(12) United States Patent
Turkyilmaz

(10) Patent No.: US 11,547,429 B2
(45) Date of Patent: Jan. 10, 2023

(54) DEVICE USED IN THE IMPLEMENTATION OF LAPAROSCOPIC HYDATID CYST OPERATIONS

(71) Applicants: Artun AG, Golcuk Kocaeli (TR); Murat Turkyilmaz, Edirne/Merkez (TR); Sena Dilek AG, Golcuk Kocaeli (TR); Zeliha Turkyilmaz, Edirne/Merkez (TR)

(72) Inventor: Zeliha Turkyilmaz, Edirne/Merkez (TR)

(73) Assignee: TRAKYA UNIVERSITESI, Edirne (TR)

(*) Notice: Subject to any disclaimer, the term of this patent is extended or adjusted under 35 U.S.C. 154(b) by 0 days.

(21) Appl. No.: 15/752,808

(22) PCT Filed: Aug. 12, 2016

(86) PCT No.: PCT/TR2016/000113
§ 371 (c)(1),
(2) Date: Feb. 14, 2018

(87) PCT Pub. No.: WO2017/030513
PCT Pub. Date: Feb. 23, 2017

(65) Prior Publication Data
US 2018/0235647 A1 Aug. 23, 2018

(30) Foreign Application Priority Data
Aug. 14, 2015 (TR) .................................. 2015/10110

(51) Int. Cl.
*A61B 17/32* (2006.01)
*A61B 17/00* (2006.01)

(52) U.S. Cl.
CPC .................. *A61B 17/32002* (2013.01); *A61B 2017/00022* (2013.01); *A61B 2017/00115* (2013.01);
(Continued)

(58) Field of Classification Search
CPC .. A61B 17/32002; A61B 2017/320024; A61B 2017/00424
See application file for complete search history.

(56) References Cited

U.S. PATENT DOCUMENTS 5,312,399 A * 5/1994 Hakky ........... A61B 17/320758
606/14
5,569,254 A * 10/1996 Carlson .............. A61B 17/1644
600/101

(Continued)

*Primary Examiner* — Sarah A Simpson
(74) *Attorney, Agent, or Firm* — Bayramoglu Law Offices LLC

(57) ABSTRACT

The present invention relates to a laparoscopic device used in laparoscopic cyst hydatid operations, which has a shaft that enables simultaneous performance of the breaking of the cyst content in the area by the blade in the conical slot at the end of the shaft, aspiration of the cyst fluid and the broken female vesicles and if required, washing processes and an electrically connected hand unit. The mentioned laparoscopic device contains a motor inside the hand unit, motor drive unit, cycle unit, cycle control unit and trigger and the shaft part contains aspiration channel, washing channel, the shaft enabling the blade movement and blade unit in the conical slot at the end part of the same shaft, which rotates transversely to the conical slot.

8 Claims, 3 Drawing Sheets

Figure 1:
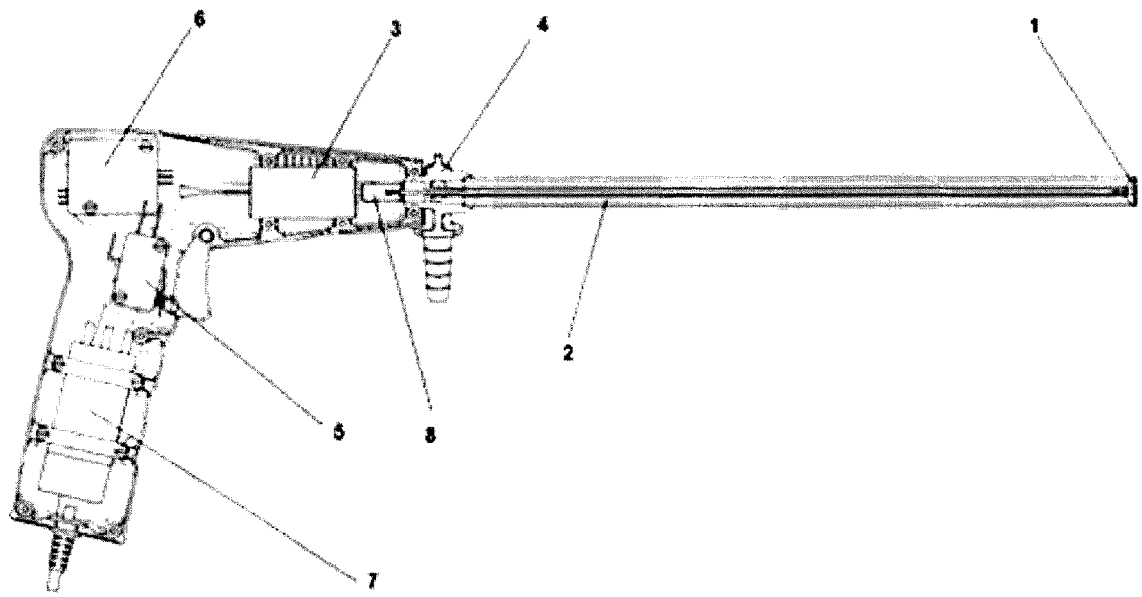

(52) U.S. Cl.
CPC ............... *A61B 2017/00424* (2013.01); *A61B 2017/320024* (2013.01); *A61B 2217/005* (2013.01); *A61B 2217/007* (2013.01)

(56) References Cited

U.S. PATENT DOCUMENTS

| | | | |
|---|---|---|---|
| 2009/0062872 A1* | 3/2009 | Chin | A61B 1/00082 606/86 R |
| 2009/0299141 A1* | 12/2009 | Downey | A61B 17/2909 600/118 |
| 2012/0209167 A1* | 8/2012 | Weber | A61B 17/3474 604/26 |

* cited by examiner

DEVICE USED IN THE IMPLEMENTATION OF LAPAROSCOPIC HYDATID CYST OPERATIONS

CROSS REFERENCE TO RELATED APPLICATIONS

This application is a national phase filing under 35 U.S.C. § 371 of International Application No. PCT/TR2016/000113 filed Aug. 12, 2016, which claims priority from Turkey application number 2015/10110, filed Aug. 14, 2015, the entire contents of which are hereby incorporated by reference herein.

DESCRIPTION

Technical Field

The invention is related to a device used in laparoscopic cyst hydatid operations.

The invention relates to a laparoscopic device having its own energy unit making the blade in the concave slot at the end of the shaft work as the cyst is crumbled and simultaneously providing the washing of the application area and the aspiration of the cystic fluid.

State of the Art

In laparoscopic surgery, the organs to be operated are made visible through a screen by a camera to be placed and the operation is carried out by the images on the screen. Since detailed images, which are 20 folds larger than those seen by a naked eye, are obtained by a camera, it is possible to see the fine details of the anatomic structures. In laparoscopic operations, $CO_2$ (carbon dioxide) gas given to the abdominal cavity with the help of cannulas (trocar) with the shape of a tube with various diameters and lengths, which is placed in the abdomen and this way, the abdominal cavity is insufflated. Accordingly, space with appropriate width is provided in the cavity formed between the abdominal organs and abdominal wall, for the operation of surgical instruments. Although the number of incisions (3-5) and the width of the incision vary based on the type of the operation, in general, the width of the incision is about 0.5-1 cm. The laparoscopic operations are generally applied under general anesthesia. The operations, same with those in the classical open surgery are performed with the instruments used by passing through trocars (cannulas in the shape of a tube). All the incisions are closed after the trocars are removed and the operation is concluded.

The cyst wall is pierced by a dissector or any manual instrument with piercing features and having connections with the cautery (hook etc.) inserted through a hole in laparoscopic cyst hydatid surgery and the fluid inside is aspirated. Afterwards, female vesicles in the cysts are taken in a single bag; the bag is puckered without contaminating the intra-abdominal area and it is pulled out. The bag used here is usually the bag which is used in gall blander operations in order to take the gall bladder out of the abdomen. In addition to these, there are some more instruments with breaker parts, which are used to facilitate the aspiration of the content of the cyst. Some of these instruments are quite bulky for the laparoscopic operations. The common characteristic of all is that the breaker part rotates vertically like a drill and breaks the content of the cyst and facilitates the aspiration. Such breaker instruments create safety concerns since they rotate vertically to the tissue (organ). Even if the breakers functioning vertically have pull-push mechanisms controllable from the handle, it is hard to claim that they are hundred percent safe. Moreover, not enough space is left for the cannula which aspirates within the same shaft, since the shafts driving the breakers are too thick. This makes the aspiration process difficult.

It is not possible to compare a successful laparoscopic operation with an open surgery in terms of the parameters such as the patient's comfort and total cost. This is because following a laparoscopic operation, a person can quickly return to his/her business life just like he/she can turn back to his/her daily life activities.

The surgeons usually try to aspirate the cyst content in a laparoscopic cyst hydatid operation through instruments which are not appropriate for the purpose. This can cause problems generally attributable to contamination during the aspiration of the cyst content. When female vesicles are directly aspirated, they block the aspirator since they have coarse particles. This slows down the speed of the process and naturally, extends the operation time. In the state of the art; even if there are a few non-professional breaker models with macro dimensions; the need for these to be positioned in the same body with the aspirator increased gradually.

In the utility model application with application no TR2013/08974; it shall be seen that there is an aspiration channel attached to the end of a drill and blade mechanism at the end of the shaft in this channel. The thickness of the blade shaft in the aspiration tube attached at the end of the device in the mentioned utility model does not leave enough space for the aspiration process, which is the general purpose. In addition, it should be taken into consideration that the blade at the end of the aspiration tube is very large and this causes blocking.

Moreover, when the utility model application with application no TR2013/08974 is examined; it shall be seen that there are two different trigger mechanisms in the device. (one trigger for taking the drill end out and another trigger for operating the drill). An application made this way, is not ergonomic and makes it difficult for the surgeon to provide the control of the device and even undesired traumas during the operation.

At the same time, the resonance increases during the operation due to the distance between the connection point of the shaft and drill and the blade part at the end of the aspiration tube and not containing a shaft channel. Moreover, a shaft passed directly through the aspiration tube, may cause aspirated fluid, broken tissue to flow back from the connection point of the drill when the aspiration is stopped and as a result may result in the risk of infection. In addition, although the mentioned utility model partly responds to the simultaneous performance of the breaking of the cyst and the aspiration procedure, it is also possible to have blocking during the aspiration process due to the direction of the breaker and its bulkiness. When the mentioned utility model is examined; it is evaluated that the end part is designed in order to break in an uncontrolled manner, not in order to perform an incision. Also, it is possible that it may damage the tissues if it moves openly in the abdomen. Since it is required that the breaker end to be taken out of the channel by a latch in a controlled manner as its rotation within the channel; undesired traumas could be resulted if the latch is touched accidentally. Hundred percent safety cannot be guaranteed for any breaker with its end outside or which rotates vertically to the tissue.

This state necessitated to develop a device which would facilitate the application especially for the liver cyst hydatid due to the insufficiency of the current solutions and to make new researches in the relevant technical field.

THE PURPOSE AND SHORT DESCRIPTION OF THE INVENTION

The purpose of the invention is to facilitate the application of laparoscopic cyst hydatid operation. The most important difficulty in the application of laparoscopic cyst hydatid operation is the unavailability of an instrument which would provide the application comfort for the process. On the other hand, if there is an appropriate device equipment (to help to facilitate the laparoscopic application) for liver cyst hydatid just like laparoscopic cholecystectomy, then laparoscopic surgery would be the golden standard.

FIGURES TO HELP UNDERSTANDING THE INVENTION

FIG. 1: is the general view of the present device used in laparoscopic cyst hydatid operations.

Figure 1B:
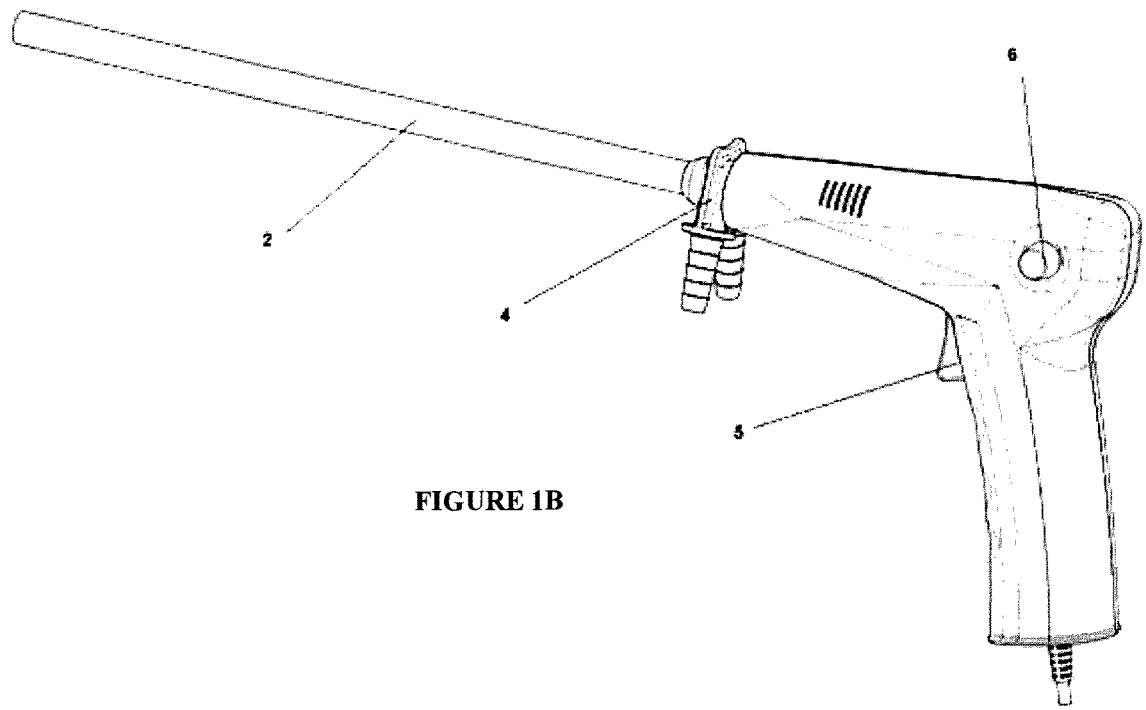

FIG. 1B: is the general view of the present device used in laparoscopic cyst hydatid operations, from another angle.

Figure 2:
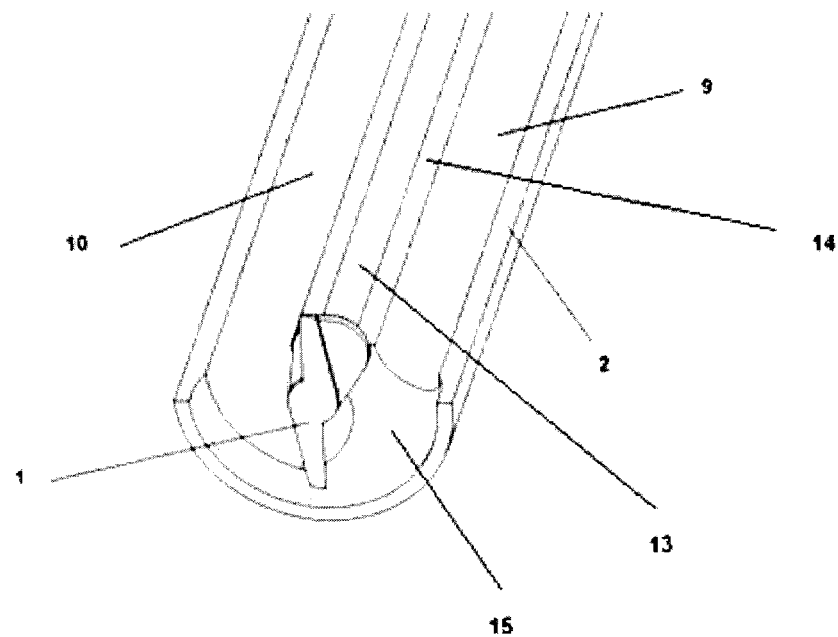

FIG. 2: is the detailed view of the shaft and concave end part of the present device.

Figure 3:
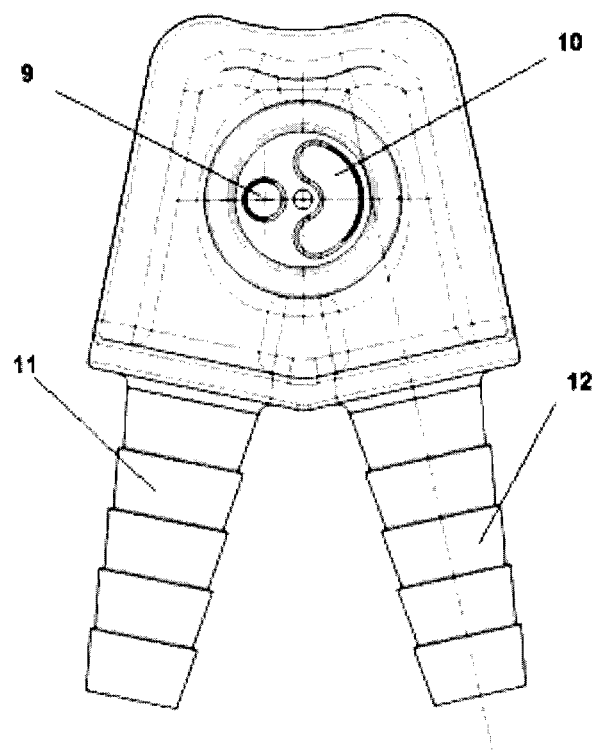

FIG. 3: is the detailed view of the washing and aspiration separator.

Figure 4:
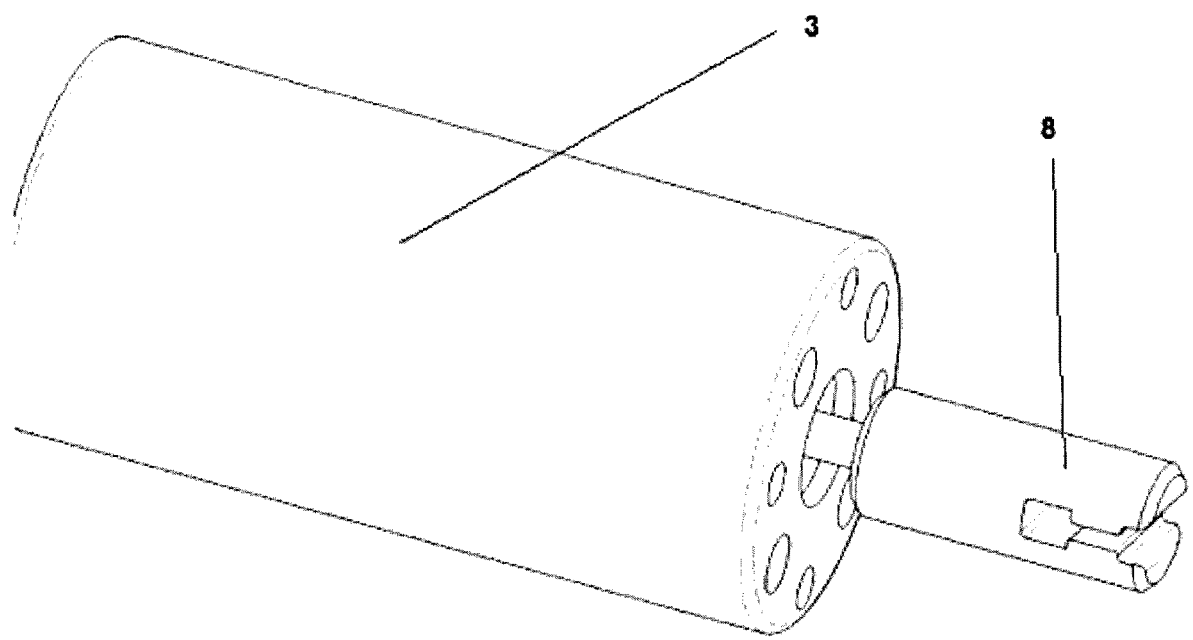

FIG. 4: motor and coupling connection

NO—NAME OF THE PART

1. Blade unit
2. Shaft
3. Drive unit
4. Separator
5. Trigger mechanism
6. Cycle control unit
7. Power source
8. Coupling
9. Washing channel
10. Aspiration channel
11. Washing inlet
12. Aspiration inlet
13. Blade shaft
14. Shaft channel
15. Concave Slot

DETAILED EXPLANATION OF THE INVENTION

In the present invention which has been developed after long researches and trials; the breaking and aspirating functions are within the same shaft (2). In addition to these, washing feature is carried out from another channel [washing channel (9)] within the mentioned shaft (2). There is at least one aspiration channel (10) opened lengthwise, at least one washing channel (9) and at least one shaft channel (14) in the mentioned shaft (2). This way, three functions are enabled with the shaft (2) reaching the application area. Our desire to include three functions (breaking, aspirating, and washing) in this device [in the shaft (2)] is due to two reasons. The first one is to complete the operation process faster and with minimum contamination without any need for inserting the instruments through the ports (incisions) many times. Another issue, which is also as important as the first one, is to advance the laparoscopic operation with the minimum number of ports in time.

The mentioned laparoscopic device is composed of two parts. The mentioned main parts are the shaft (2) and the device body. There is a power source (7), cycle control unit (6), trigger mechanism (5), coupling (8) and drive unit (3) on the body of the device which is in the form of a handle. There is at least one (pneumatic or hydraulic drive system, electric motor, electronic motor etc.) drive unit (3) on the body of the device. The energy required for the mentioned drive unit (3) is provided from a power source (7). The mentioned power source (7) can be an electricity line, battery, accumulator etc. The operation of the drive unit (3) can be followed up by the warning sounds within the structure of the device.

The shaft (2) is generally a cylindrical part where the end is as a concave structure. The shaft (2) is connected to the body of the device by a separator (4), from its end which is not in concave structure. There are at least three channels in the shaft (2) which are opened lengthwise. The mentioned channels are at least one aspiration channel (10), at least one washing channel (9) and shaft channel (14). There is a blade shaft (13) in the shaft channel (14). The end of the blade shaft (13) at the side of the device body is connected to the drive unit (3) by means of a coupling (8). There is a blade unit (1) at the other end of the blade shaft (13). The blade unit (1) operates in the concave slot (15) of the shaft (2). Aspiration channel (10) is connected to the aspiration inlet (12) within the structure of the separator (4). The fluid and particles sucked into the aspiration channel (10) at the end of the aspiration process are taken from the aspiration inlet (12). The aspiration inlet (12) is attachable to the aspiration devices available at the operating rooms.

The washing channel (9) is connected to the washing inlet (11) within the structure of the separator (4). This way, the fluid required for the washing process can be given to the washing channel (9) from the washing inlet (11). The washing inlet (11) is attachable to the aspiration devices available at the operating rooms. The separator (4) is detachable from the device body. Moreover, the shaft (2) is also attachable-detachable to the device body.

There is a completely empty space at the middle section of the shaft (2) for the blade shaft (13) between the drive mechanism (3) of the device and the blade unit (1). This space is named as the shaft channel (14). The shaft channel (4) provides the blade unit (1) to operate at the desired level without any roll. The rotating motion transferred to the coupling (8) from the drive mechanism (3) is transferred to the blade shaft (13) without any roll. The blade unit (1) rotates together with the blade shaft (13). The blade unit (1) makes a transverse turn according to the shaft (2), in the concave end part (15) of the shaft (2). This way, the blade unit (1) rotates in a safe and controlled manner in the concave end part (15). The aspiration channel (10) and the washing channel (11) also open up to inside of the mentioned concave slot (15). In FIG. 2, the cross-section of the shaft (2) enabling the breaking, washing and aspirating processes can be seen. Aspiration channel (10) is wider than the washing channel (9) in order to enable the passage of the cyst particles.

Thanks to the separator (4), it is enabled that the fluid given out for the washing process and the fluid received in the device for the aspiration fluid proceed in different channels over the same mechanism, without mixing. It contributes considerably to the ergonomics that the aspiration inlet (12) and the washing inlet (11) are facing downwards and upwards at the connection section.

Moreover, the concave end part (15) of the shaft (2) is designed as a concave inner structure where the breaking, washing and aspirating procedures can be carried out. This feature of the device, enables the blade unit (1) (breaker) not to contact the wall within the cyst pouch. The design of the concave end part (15) of the mentioned shaft (2) is the most important safety key for prevention of the liver trauma during the process. In the present device; the safety is considered as much as simultaneous performance of the three functions (breaking, aspirating and washing). Blade units (1) of different forms can be used in the mentioned device. Blade unit (1) replacement can be carried out from the concave slot (15) of the shaft (2).

In addition to safety, the ergonomics of the hand instruments is one of the most important issues for the surgeons. In this regard, the device has a handle which the surgeons who are accustomed to performing laparoscopic cholecyctectomy can easily adapt to and work comfortably. For disinfection, the device is designed in a manner to be disinfected by dismantling the shaft (2) part completely from the handle. There are no structures within the power unit and drive mechanism (3) of the device which would endanger the sterilization. There is a cycle control unit (6) on the device. The speed control of the rotation of the blade unit (1) at the end of the shaft (2) is provided by the mentioned cycle control unit (6). Laparoscopic device has a titanium coupling (8) which provides the connection between the shaft (2) and drive mechanism (3) with its special lock system and prevents undesired vibrations by its structure, thus provides the safe operation of the blade.

The operation of the laparoscopic device is as follows;

In laparoscopic cyst hydatid operations: specifically in the process of removing the female vesicles away from the area of application by aspiration procedure; aspiration channels and tubes may be blocked due to the large size of the female vesicles. The present invention enables the female vesicles with large particles, to be grinded at the same time with the aspiration process, by the help of the blade unit (1), which is placed in the concave end part (15) of the shaft (in the conical slot) and which operates (rotates) horizontally (transversely). This way, blocking of the aspiration channels (10) during the aspiration process is prevented. The movement of the present invention is provided by the transfer of energy from any power source (7) to the drive mechanism (3). The trigger mechanism (5) and cycle control unit (6) are two important parts used in adjustment of the rotation speed of the blade unit (1) rotating in the conical slot. The vesicles grinded by the blade unit (1) located at the concave end part (15) of the shaft (2) which accommodates washing channel (9), aspiration channel (10 and shaft channel (14) within its structure are absorbed from the aspiration channel (10) and are transferred to the aspiration inlet (12) of the separator (4). At the same time, the fluid from the washing inlet (11) of the separator is used in the washing of the application area with the help of the washing channel (9) in the shaft (2).

What is claimed is:

1. A laparoscopic device used in an application of laparoscopic cyst hydatid operations, wherein the laparoscopic device provides a simultaneous performance of a washing procedure, a breaking procedure and an aspirating procedure of an operation area, and the laparoscopic device comprises:
   a device body with at least one drive unit, wherein the at least one drive unit emits warning sounds when in operation,
   at least one shaft connected to the device body and with a concave slot at one end, wherein the concave slot is an inner structure within the at least one shaft formed by inner surfaces of the at least one shaft,
   at least one washing channel in the at least one shaft, opened lengthwise,
   at least one aspiration channel in the at least one shaft, opened lengthwise,
   at least one shaft channel in the at least one shaft, opened lengthwise,
   at least one blade shaft in the at least one shaft channel, wherein the at least one blade shaft transfers spin movement received from the at least one drive unit to a blade unit operating at one end of the at least one blade shaft,
   wherein the blade unit is positioned in and operates in the concave slot of the at least one shaft, the at least one shaft completely surrounds a periphery of the blade unit and the at least one blade shaft, and the blade unit spins transversely to the at least one shaft in the concave slot with a movement received from the at least one blade shaft;
   wherein the at least one washing channel, the at least one aspiration channel and the at least one blade shaft are provided alongside of each other in the at least one shaft, the at least one blade shaft is provided in a middle of the at least one shaft between the at least one washing channel and the at least one aspiration channel, and the at least one blade shaft, the at least one washing channel and the at least one aspiration channel each independently extend along a longitudinal axis of the at least one shaft to provide the simultaneous performance of the washing procedure, the breaking procedure and the aspirating procedure,
   wherein the at least one aspiration channel is wider than the at least one washing channel.

2. The laparoscopic device of claim 1, wherein the at least one shaft has a diameter of 9.5-11.5 mm and a length of 250-350 mm.

3. The laparoscopic device of claim 1, further comprising at least one coupling providing a connection between the at least one shaft and the at least one drive unit.

4. The laparoscopic device of claim 1, wherein the blade unit is prepared in various forms to respond to different needs of the breaking procedure to provide a breaking of a hydatid cyst.

5. The laparoscopic device of claim 1, wherein the concave slot prevents the blade unit to touch a wall in a cyst pouch during the breaking procedure, and the concave slot is designed with a concave inner structure.

6. The laparoscopic device of claim 1, further comprising a cycle control unit adjusting a speed of the at least one drive unit.

7. The laparoscopic device of claim 1, wherein the at least one shaft is connected to the device body by a separator, the at least one aspiration channel is connected to an aspiration inlet within a structure of the separator, the at least one washing channel is connected to a washing inlet within the structure of the separator, and the separator is detachable from the device body.

8. The laparoscopic device of claim 1, wherein the at least one aspiration channel has a cross-section in a shape of a kidney bean, the at least one washing channel has a cross-section in a shape of a circle, the at least one blade shaft as a cross-section in a shape of a circle, the at least one aspiration channel has a cross-sectional dimension that is larger than a cross-sectional dimension than the at least one blade shaft, the at least one washing channel has a cross-sectional dimension that is larger than the cross-sectional dimension of the at least one blade shaft, the at least one aspiration channel partially surrounds the at least one blade shaft, and the at least one blade shaft is positioned between the at least one washing channel and the at least one aspiration channel.

* * * * *